US00PP34669P2

(12) United States Plant Patent
McGhie

(10) Patent No.: US PP34,669 P2
(45) Date of Patent: Oct. 18, 2022

(54) GINGER PLANT NAMED 'MCGHIEVCG'

(50) Latin Name: *Alpinia officinarum*
Varietal Denomination: McghieVCG

(71) Applicant: Errol Anthony McGhie, St. Catherine (JM)

(72) Inventor: Errol Anthony McGhie, St. Catherine (JM)

( * ) Notice: Subject to any disclaimer, the term of this patent is extended or adjusted under 35 U.S.C. 154(b) by 0 days.

(21) Appl. No.: 17/485,845

(22) Filed: Sep. 27, 2021

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Klarquist Sparkman, LLP

(57) ABSTRACT

A new plant variety of the Zingerberacae family resulting from a discovery of a mutant attached to a stool (mat) of 'McghieJCG' (*Alpinia officinarum*) in a cultivated field and subsequently asexually reproduced from stem cuttings. The most distinguishing characteristics of this new variety is the pattern-gene fishbone leaf variegation and the pungent cinnamon fragrance and flavor of its leaves (tea). The new variety has valuable commercial potential and excellent post harvest prospects.

7 Drawing Sheets

Botanical denomination: *Alpinia officinarum.*
Variety designation: 'McghieVCG'.

BACKGROUND OF INVENTION

The present invention relates to a new and distinct variety of the Zingerberacae family. The new variety is named 'McghieVCG', (trade name Mcghie Variegated Cinnamon Ginger). The new variety originated as a discovery of dominant yellow-green variegated leaves growing from a 'McghieJCG' (U.S. Plant Pat. No. 26,408) plant in a cultivated field (open sun), situated in the suburb of the town of Bog Walk in the parish of St. Catherine, Jamaica W.I.

'McghieVCG' is most similar to its parent (mother) plant 'McghieJCG'. The new variety develops into a fairly large mat with well-defined pseudo-stems bearing medium to large lanceolate leaves with prominent chlorophyll pattern-gene fishbone variegation. In contrast, 'McghieJCG' has little to no pattern-gene variegation of its leaves and distinct elliptic shape especially in later leaves.

The first observation of the 'McghieVCG' plant was in July 2019.

'McghieVCG' was asexually reproduced in Bog Walk by means of stem cuttings and subsequently reproduced over three (3) generations of new plants. The distinguishing characteristics of 'McghieVCG' have been retained through successive generations.

Growth was observed at eighteen (18) months and the plants exhibited consistent stable, healthy and vigorous growth characteristics with its roots, stems and leaves (entire plant) appearing to be disease free/pest resistant for the entire period of growth.

'McghieVCG' was asexually reproduced under different natural conditions; including partial cover, full cover, and full sunlight employing similar cultivation practices as per the mother plant ('McghieJCG'); i.e. fertile, moist, and well drained soils employing the use of organic manure and moderate watering. 'McghieVCG' plants were also cultivated in pots under full and partial cover in the open field. It was observed that the best growth occurred in plants grown in the open field with partial cover or full cover.

It was also observed that like the mother plant, 'McghieJCG', the leaves of the new variety had a pungent cinnamon-like scent.

There are also significant physical differences between the leaves of the new plant and its mother parent. For example, 'McghieVCG' has moderate olive-green leaves with distinct strong yellow variegation. In contrast, 'McghieVCG' has greyish olive-green leaves with little to no variegation (Table 2).

As a horticultural plant, 'McghieVCG' exhibits adaptability as a natural indoor and outdoor plant and also because of its versatile growth patterns when grown under different environmental conditions, in pots or open fields. Other characteristics of 'McghieVCG', such as its hardiness, attractiveness and general canopy, demonstrates it as a suitable plant for commercial production for the horticultural industry.

The absence of any traces of diseases/insects/and pests at this stage of its growth if maintained will also recommend it as an important agricultural plant in various crop protection programs such as barrier crops, inter-cropping, multi-cropping and landscaping.

'McghieVCG' can be grown as an herb/spice in home gardens.

BRIEF DESCRIPTION OF THE DRAWINGS

The accompanying drawings consist of color photographs showing the new plant variety form at eighteen (18) months along with, the mature plants in a commercial cultivated nursery in Bog Walk, depicting fields of asexually produced new plants of 'McghieVCG'. Other pictures show prominent leaf variegation of the new plant variety.

DETAILED PLANT DESCRIPTION

Figure 1:
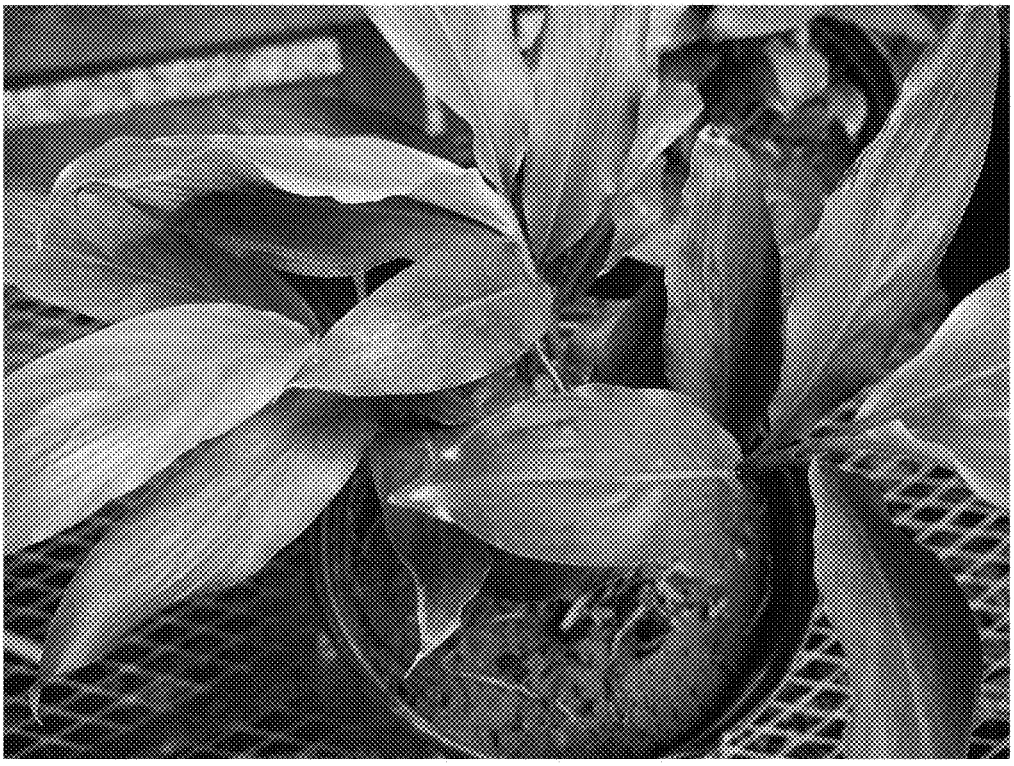
FIGS. 1-3 show a perspective view of a potted plant of the new plant variety 'McghieVCG' illustrating the overall form and appearance of the plant at eighteen (18) months.
Figure 2:
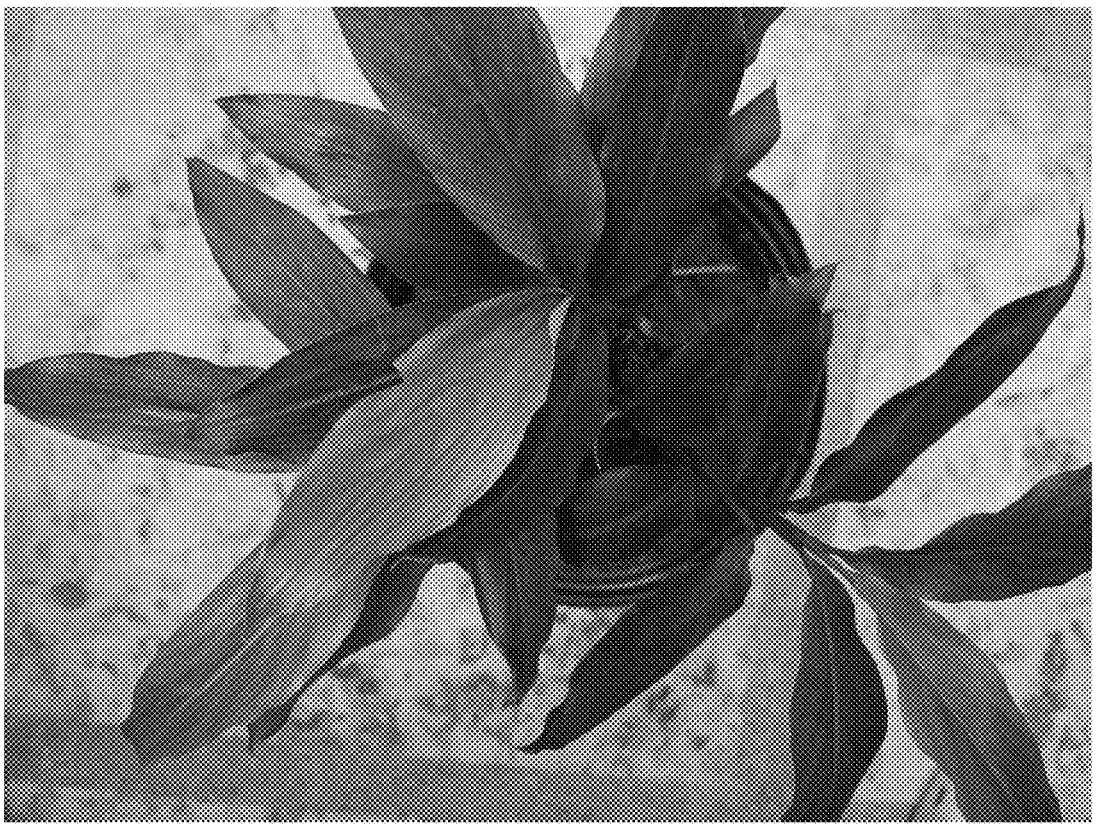
Figure 3:
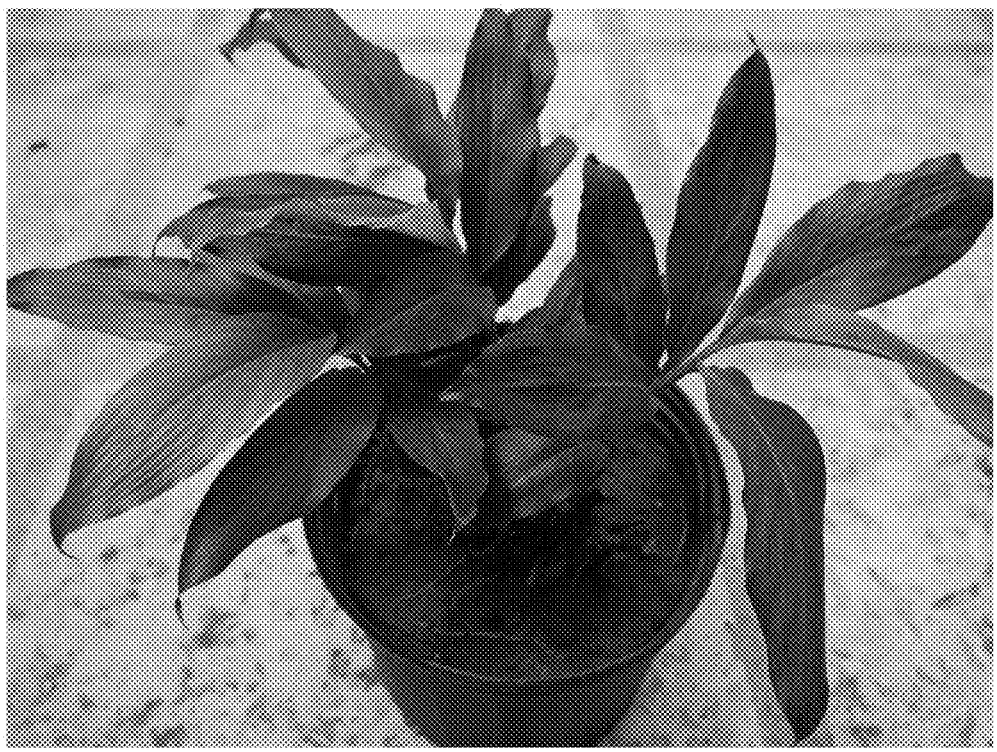
Figure 4:
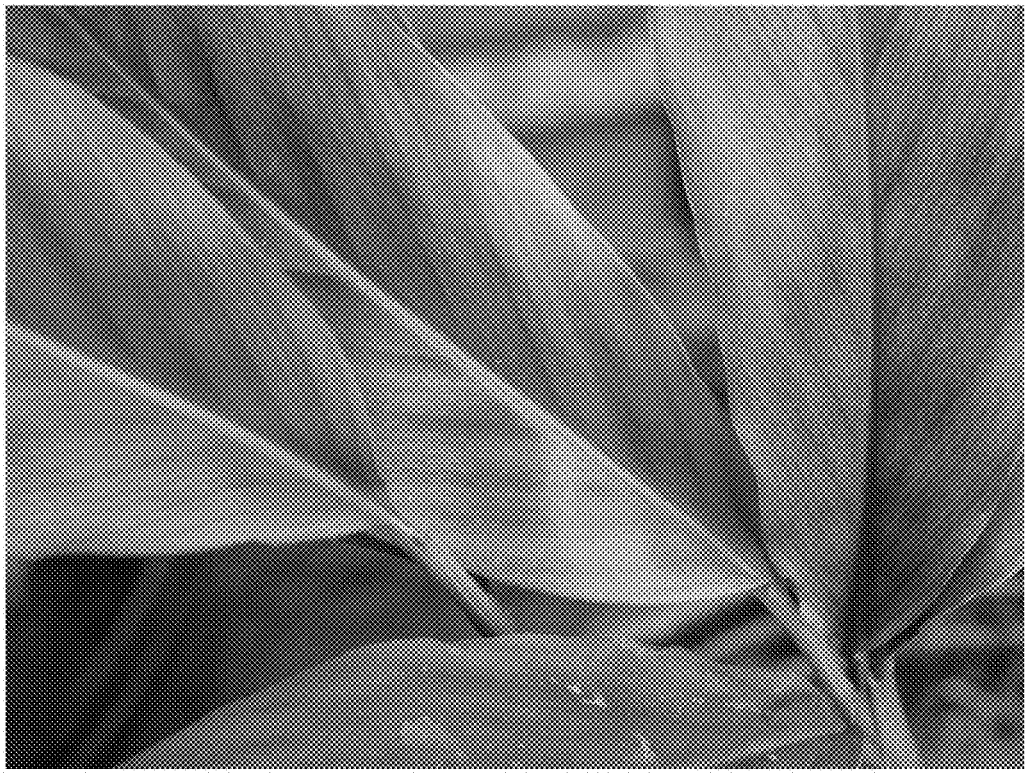
FIG. 4 shows a perspective view of leaf variegation of a potted plant of the new plant variety 'McghieVCG' grown at eighteen (18) months.
Figure 5:
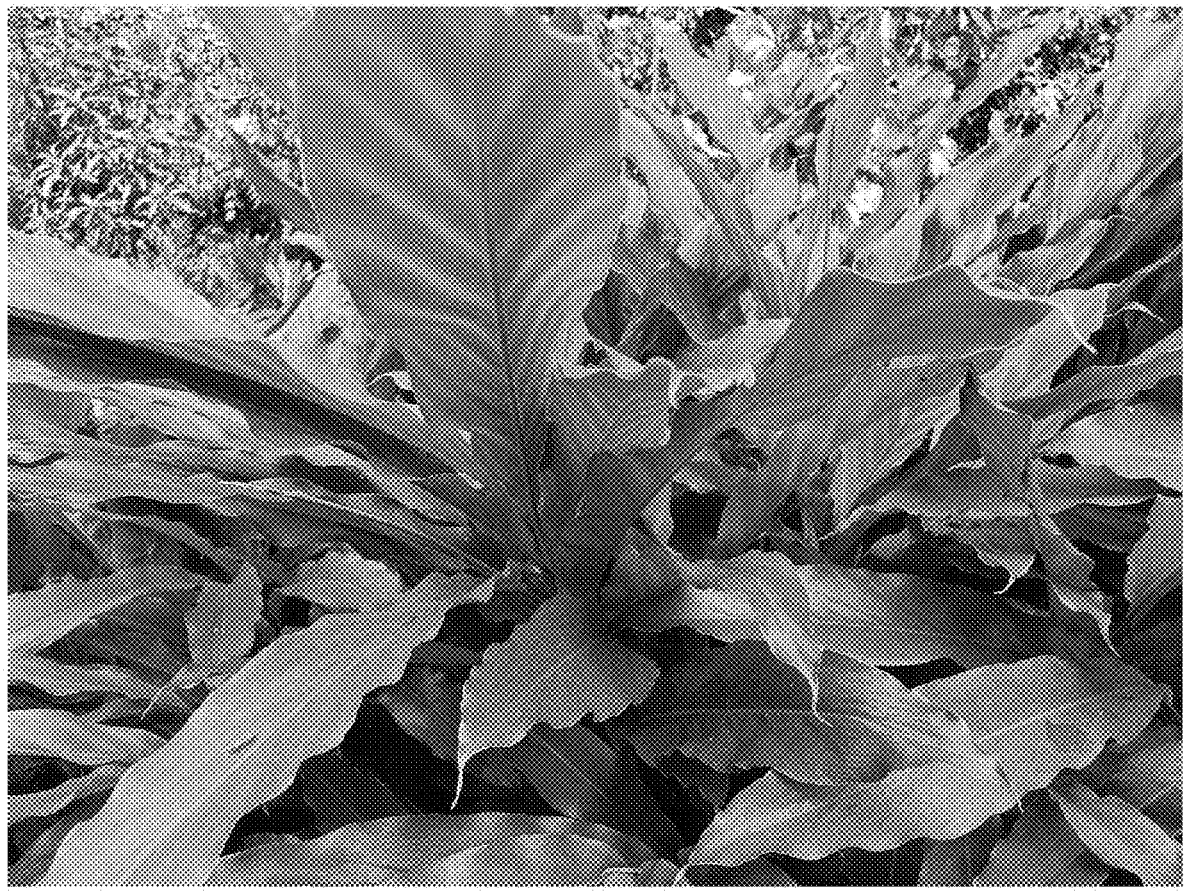
FIG. 5 shows a perspective view of prominent leaf variegation of mature leaves of the new plant variety 'McghieVCG' grown in open field in a commercial nursery.
Figure 6:
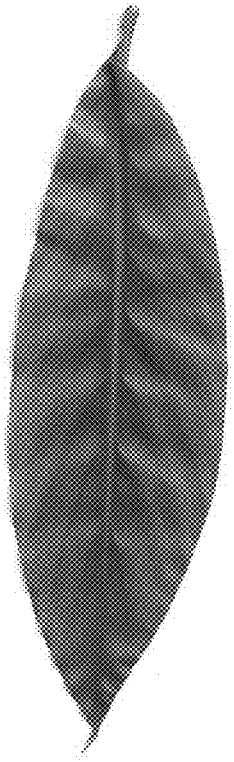
FIG. 6 shows a scanned image of the lanceolate pattern-gene foliar variegation of leaf from a potted plant at eighteen (18) months of the new plant variety 'McghieVCG'.
Figure 7:
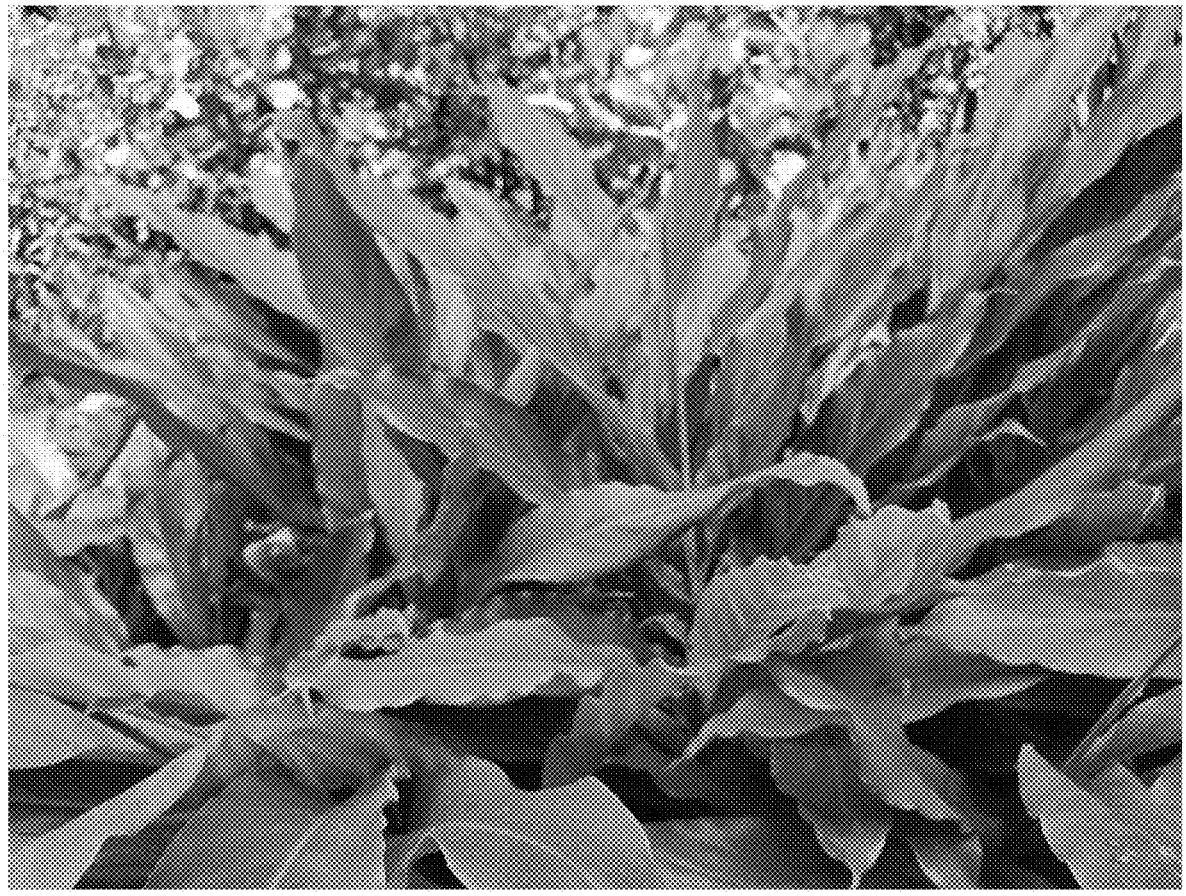
FIG. 7 shows an asexually reproduced plant of 'McghieVCG' growing in an open field in a commercial nursery.
Figure 8:
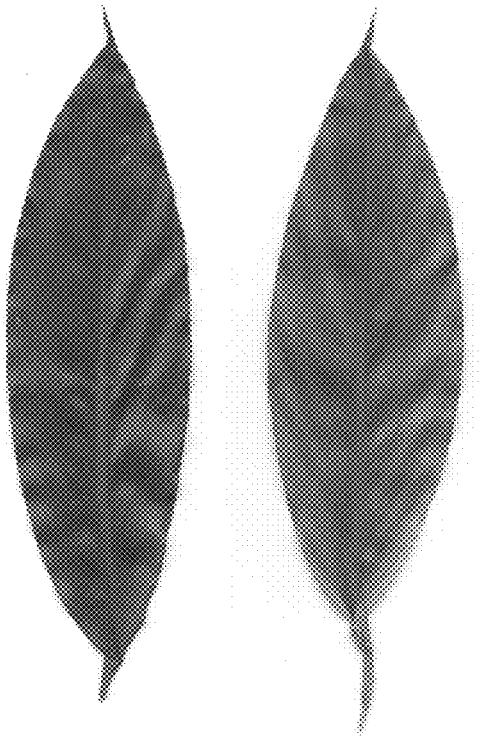
FIG. 8 shows a side-by-side comparison of pattern gene foliar variegation of a leaf from a potted 'McghieJCG' (left) and 'McghieVCG' (right) plant at eighteen (18) months.
Figure 9:
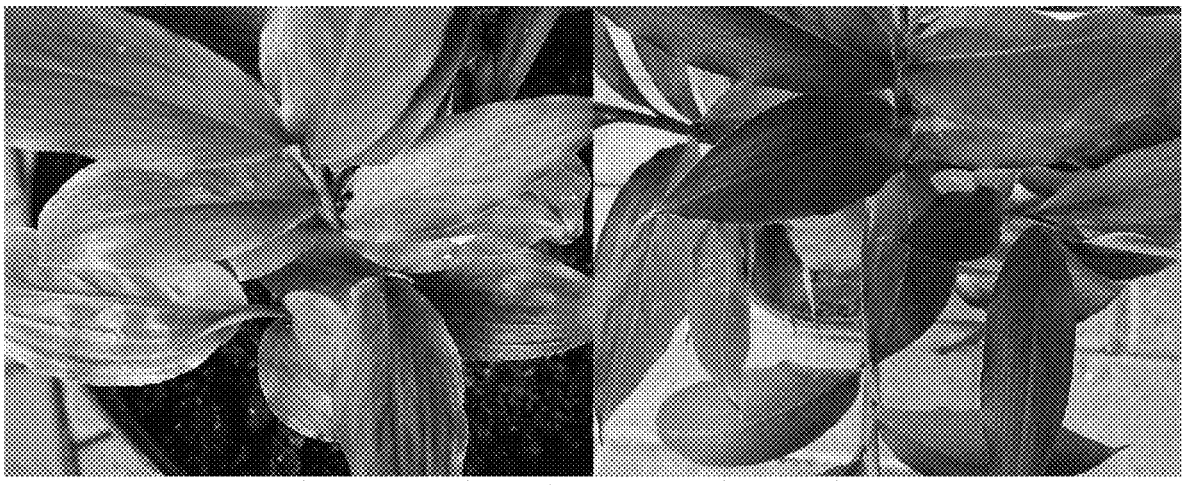
FIG. 9 shows a side-by-side perspective view of 'McghieVCG' (left) and 'McghieJCG' (right) showing difference in foliar color and variegation.

The following is a detailed description of 'McghieVCG' based on plants observed after eighteen (18) months growth in the open field under partial cover. The new variety has been observed under direct and partial sun environmental conditions. Color designation and other values stated may deviate slightly from stated values due to seasonal changes but the deviations will be within the range expected from varying environmental conditions. Color designations were referenced employing The Royal Horticultural Society Colour Chart 6$^{th}$ Edition 2015.

'McghieVCG' can be described as an evergreen at this stage of its growth with prominent foliar pattern-gene (natural) fishbone variegations in in shades of green and yellow-green. This color varies according to light intensity and maturity of leaves. The color/shade of the leaves when grown in partial lighting or direct lighting is moderate olive-green 137A with strong yellow-Green 144A, 144B and 145A variegation. The color/shade of stem in partial or direct lighting condition is strong yellow-green 143C.

A stem cutting from the rhizome of the mother plant 'McghieJCG' with the mutant 'McghieVCG' attached was transplanted to a pot containing a special organic potting mixture of sandy loam soil and compost mix and placed under partial cover and grown for two months employing moderate watering. Stem cuttings from a resulting batch of six plants were obtained and transplanted to a specially prepared bed in the open field using a similar plant medium. The procedure was repeated at four months from a new batch of 42 plants. Some plants were also transplanted in specially prepared pots with a similar plant medium and placed under partial and full cover in the open field. This procedure continued at six and eight month intervals with some plants transplanted in beds with no cover. The plants were observed to grow more vigorously in the open field under partial cover especially during periods of sustained rainfall. Average growth gain observed every two months over the eight month period was eight new plants.

Origin: Stem cutting (rhizome division) performed on a plant obtained from Bogwalk, St. Catherine Jamaica.

Parentage: 'McghieJCG' (female parent).

Family: Zingerberacae.

Genus/species: *Alpinia officinarum.*

Bouquet: Aromatic and cinnamon like.

Flavor: Aromatic and cinnamon like.

Commercial: Agriculture, horticulture, herb, spice, essential oils, extracts.

Form: Perennial herb with short highly branched rhizomes which eventually give rise to a high density of tillers. General vertical growth pattern of pseudo stems and shoot growth is similar to flexibility, firmness, structure and growth rate to 'McghieJCG'. Shoot display heterophylly (different shapes depending on the age, varying between lanceolate and occasional elliptic). Leaves are distichously.

The following describes the growth parameters of a potted 'McghieVCG' plant at 18 months of age.

Younger leaves: The first three to four leaves trend toward lanceolate with acuminate leaf apex. Average leaf is 3.2 cm in diameter and 8.95 cm long. Ligules are indistinct, or can be regarded as absent.

Later leaves: The leaves that develop after first three to four leaves. Shape is distinctly lanceolate; leaf base is attenuate or very slightly etiolate (grooved petiole—0.3 cm long), and ligules are absent.

Lamina/blade: Average length for leaf shapes is (14.1 cm).

Leaf margin: Entire. Generally, leaf margins remain consistent at all stages of growth.

Leaf apex: Acuminate.

Leaf surface: Upper and lower surface are smooth.

Leaf midrib: Grooved and rounded.

Leaf angle: Earlier leaves are generally oblique but as later leaves undergo elongation to be more elliptic, the angle is reduced and leaf tips bend and point downward.

Leaf sheath coloration: Outer upper margins (where ligules would be) are Dark Greyish Red N186C (Greyed-Purple Group) and leaf sheath extens a little beyond the point of leaf attachment.

Phyllotaxy (leaf arrangement): Alternate.

Petiole: Not distinct as they are all tightly bundled to form the pseudo stem (supporting structure of the plant).

Rhizome: Cylindrical in shape and it produces an average of 5 buds which eventually develop into mature rhizomes with their correspondent aerial pseudo stems and leaves etc. Average length: 10 cm or 4 inches. Average width: 1.4 cm or ½ inch. Color Greyed-Yellow Group Pale Yellow (161D) with Grey Orange Group Brownish Orange (166C).

Fragrance description: Fragrance of leaves may be described as a moderate spicy fragrant blend of leaf cinnamon, ginger and lemon (with no lingering sensation or feeling on nasal and throat mucosa).

Leaf fragrance detection: Held closely to the nostrils without rubbing or crushing of green excised leaves, the emanated fragrance is detected readily from the upper surface of the leaf. When leaf is manipulated (crushed) or cut there is a pungent cinnamon fragrance that emanates from the leaf with traces of other fragrances. These fragrances are more pronounced in the leaves of plants grown in higher light intensities.

Flowers, fruit, seeds and reproductive organs have not been observed with the new variety.

Figure 10:
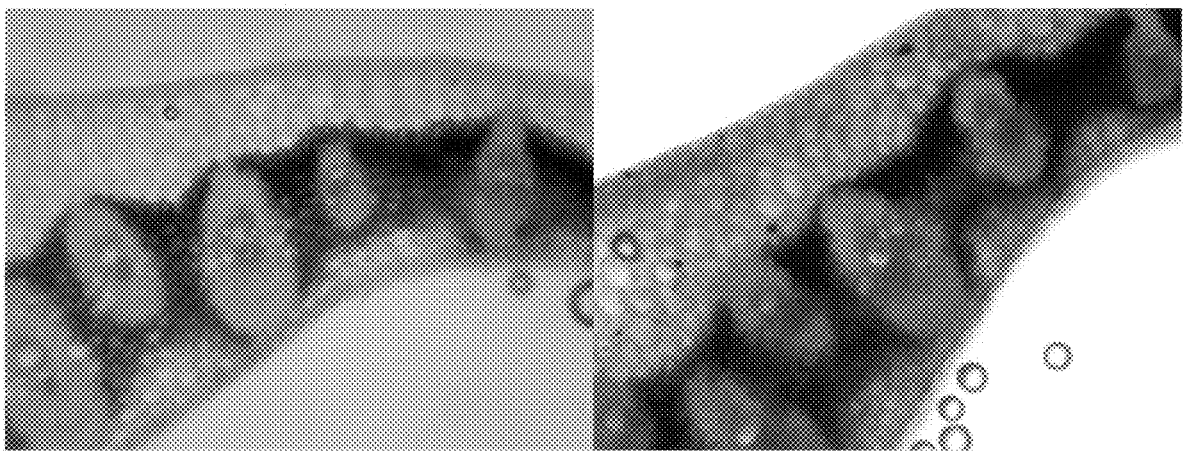
FIG. 10 shows a transverse section of 'McghieVCG' at 40× magnification in distilled water (left) and iodine (right) showing bundle sheath of leaf with pinnate venation.

Venation: Leaves display pinnate patterns of venation with distinct variegation in leaf color of Moderate Olive Green 137A with Strong Yellow-Green 144A, 144B and 145A variegation (also see FIG. 10).

Pubescence: Absent.

Growth parameters of an 18 month 'McghieVCG' plant in the Jamaican humid tropics is shown in Table 1 below.

TABLE 1

'McghieVCG' Growth Parameters

| Parameter | Measurement (cm) |
|---|---|
| Average leaf length (Upper*) | (13.5-14.9) 14.1 |
| Average leaf length (Lower**) | (6.7-11.4) 8.9 |
| Average leaf width (Upper) | (3.6-4.5) 4.2 |
| Average leaf width (Lower) | (1.9-4.1) 3.2 |
| Average leaf shoot height | (37.0-38.1) 37.4 |
| Stool (mat) Diameter (Canopy to leaf tip). | 51.6 |

*Measurement from the Apex of the leaf, sheath of the third fully formed (expanded) leaf from the top down

**Measured at the 6th leaf from the upper leaf.

A comparison between 'McghieJCG' and 'McghieVCG' is shown in Table 2.

TABLE 2

'Comparison of distinguishing characteristics for 'McghieJCG' and 'McghieVCG'

| Characteristic | 'McghieJCG' | 'McghieVCG' |
|---|---|---|
| Foliar Color | Shades of Grayish Olive Green (NN137) | Moderate olive-green 137A |
| Foliar Variegation | Little to no variegation | Prominent pattern gene variegation in shades of strong yellow Green 144A, 144B and 145A |
| Foliar Shape (Later Leaves) | Lanceolate | Tend toward elliptic |

Ecological & Environmental Conditions Relevant To Growth of 'McghieVCG'

Temperature: Daytime temperature ranges from 21° C.-32° C. (70° F.-90° F.), with lower temperatures during the cool seasons and nights.

Humidity: Relative humidity ranges from 85-95%.

Rainfall: Annual rain fall averages from 2000 mn-2500 mm (80-100 inches) and is evenly distributed throughout each year. The observation of the adequately fertilized plants may deviate in varying degrees from the stated parameters of the potted plants at specified periods of growth, but the deviations will be in the range expected from the varying environmental, seasonal and collateral conditions.

Soil type: Sandy and clay loam.

Habitat: The cultivated field serves as a dual purpose home garden and commercial nursery.

Other plants grown in the same habitat: Ginger family—Varying herbs/spices namely, Turmeric, Curcuma, *Alpinia galangal* and *Alpinia officinarum. Kempheria galangal, Alpinia purpurata* and miscellaneous plants of other families e.g., young cinnamon trees, bananas, citrus, plantains, mint, fever grass, and other agricultural perennials.

DEFINITIONS AND NOTIONS TO THE ABOVE DESCRIPTIONS

Elliptic: Broadest at the middle, with length usually more than twice the width.

Lanceolate: Narrow and the base, tapering toward the apex.

Accumulates: A gradually tapering to a prolonged point with two margins pinches slightly before reaching the tip. The tip maybe short or long and narrow or broad.

Glabrous: No hair present; smooth and free hairs.

Leaf measurement: This was taken pseudostems from (a). The third fully formed leaf (from short apex) and (b) the sixth leaf from the form.

I claim:

1. A new and distinct *Alpinia officinarum* plant named 'MCGHIEVCG', as herein illustrated and described.

* * * * *